United States Patent [19]

Stanislaus et al.

[11] Patent Number: 4,704,406

[45] Date of Patent: Nov. 3, 1987

[54] SPRAYABLE PHARMACEUTICAL COMPOSITION FOR TOPICAL USE

[75] Inventors: Friedrich Stanislaus, Munich; Josef M. Hofer, Kirchseeon; Axel Knoch, Munich, all of Fed. Rep. of Germany

[73] Assignee: Klinge Pharma GmbH, Munich, Fed. Rep. of Germany

[21] Appl. No.: 877,731

[22] Filed: Jun. 24, 1986

[30] Foreign Application Priority Data

Jun. 24, 1985 [DE] Fed. Rep. of Germany ....... 3522550

[51] Int. Cl.$^4$ .................... A61K 31/19; A61K 31/185
[52] U.S. Cl. ...................................... 514/570; 514/576
[58] Field of Search ................................. 514/570, 576

[56] References Cited

U.S. PATENT DOCUMENTS

| | | | |
|---|---|---|---|
| 4,489,080 | 12/1984 | Lomen | 514/282 |
| 4,525,348 | 6/1985 | Arizono et al. | 424/81 |
| 4,533,546 | 8/1985 | Kishi et al. | 424/81 |

Primary Examiner—Stanley J. Friedman
Attorney, Agent, or Firm—Burns, Doane, Swecker & Mathis

[57] ABSTRACT

Sprayable pharmaceutical preparations with an arylalkanoic acid or its salts as the active agent, suitable for topical application, containing as solvent a mixture of one or more volatile solvents and one or more nonvolatile solvents in the weight ratio range of 1:1 to 20:1. They are especially suitable for the treatment of traumatic and rheumatic diseases.

16 Claims, No Drawings

SPRAYABLE PHARMACEUTICAL COMPOSITION FOR TOPICAL USE

BACKGROUND OF THE INVENTION

The present invention relates to a sprayable pharmaceutical composition for topical use.

Therapy with topically applied pharmaceutical compositions is particularly useful when the site of application and the disease process are located in close proximity. Thus, active agents for percutaneous treatment of rheumatic or traumatic conditions are frequently put into formulations such as plasters, salves, creams, gels, emulsions, or suspensions.

These topical dosages have a series of disadvantages; overcoming these disadvantages would signify an advance in pharmaceutical development. Frequently numerous adjuvants must be added to these preparations, which leads to an unnecessary burden to the organism. In spite of the many additives used these formulations are not sufficiently stable at elevated temperatures. This leads to a "breaking" of the formulation, producing an non-homogeneous mixture of the different components of the preparation, and loss of therapeutic usefulness. This applies particularly to preparations in the form of emulsions or other dispersions.

With the currently customary topical dosage forms such as emulsions, suspensions, etc. the active material is involved in special transport and distribution processes before it can penetrate through the skin into the body and become effective.

SUMMARY OF THE INVENTION

The present invention is a sprayable preparation for topical application of pharmaceutical agents containing an arylalkanoic acid or its salts as the active agent. The preparation includes a solvent mixture consisting of (a) at least one volatile, physiologically compatible solvent, and (b) at least one non-volatile physiologically compatible solvent, the weight ratio of a:b being from about 1:1 to about 20:1.

DETAILED DESCRIPTION OF THE INVENTION

It has now been recognized that a particularly efficaceous topical preparation is obtained when the active agent is dissolved in a mixture of a volatile physiologically compatible solvent and a non-volatile physiologically compatible solvent. After evaporation of the volatile solvent, the active agent remains on the skin, dissolved in the non-volatile solvent, in an enriched form and can therefore be better absorbed. When, for example, a volatile alcohol is used as the only solvent, some of the active agent remains on the skin as a solid which leads to incomplete absorption.

According to the present invention the ratio of volatile to non-volatile solvents in the sprayable preparation should be in the range of 1:1 to 20:1, by weight. The optimum ratio for a particular active agent can be readily determined by a few simple experiments, as can the optimum concentration of active agent in the formulation; the optimized formulation will produce a highly concentrated solution of the active agent on the skin, which favors penetration and absorption.

Adhesion to the skin is enhanced by addition of a film former which is soluble in the solvents used. Polyacrylates are particularly suitable as film formers. Absorption can be delayed, and a reservoir action obtained, by selecting the type and concentration of the film former. The extent of percutaneous absorption of a particular active agent can be easily controlled by applying the formulation to a smaller or larger area.

The invention is particularly suitable for spray formulations of anti-inflammatory arylalkanoic acids such as DICLOFENAC, FENOPROFEN, FLURBIPROFEN, IBUPROFEN, NAPROXEN or KETOPROFEN, as well as their salts. These agents penetrate through skin adequately, can be applied close to the affected body area, and reach effectiveness quickly. Such active agents are typically used at a concentration between about 0.1 and 10% by weight.

The preferred volatile solvents are ethanol, propanol and isopropanol. The preferred non-volatile components are higher mono- and poly-functional alcohols, or esters of polyhydroxy acids.

As non-essential components of the formulation according to this invention, the following may be included:

(a) propellants, e.g., fluorinated chlorohydrocarbons,
(b) penetration enhancers, e.g., dimethylsulfoxide, as well as
(c) stabilizers, e.g., butylhydroxyanisole.

High dosage accuracy can be obtained when the formulations according to this invention are dispensed via specialized dosage regulators, such as pump vaporizers. Touchfree application is an advantage perceived as particularly pleasant by patients with localized, superficial pain. The rapid evaporation of the volatile component of the formulation applied to the affected area produces a pain-reducing cooling effect. At the same time, the active agent is enriched in the non-volatile solvent fraction, so that a higher concentration is available for absorption.

The pharmaceutical formulations according to this invention can be used for external treatment of pain, inflammation and/or rheumatic diseases of warm-blooded animals. They are particularly suitable for the treatment of sport- and accidental injuries such as bruises, sprains and strains; also for the supportive treatment of muscle rheumatism, painful degenerative joint diseases (arthritis), inflammatory rheumatic diseases of the joints and vertebrae, swelling, etc.; inflammation of soft tissues associated with joints (e.g. sinovial membrane, ligament, sinovial capsule, tendon and cartilage), shoulder stiffness, lower back pain, and lumbago.

The following examples further illustrate the invention; they should not be taken as limiting its scope.

EXAMPLE 1

Spray preparation containino DICLOFENAC-SODIUM 1 kg DICLOFENAC-SODIUM is dissolved in 5 kg propylene glycol, then mixed with 44 kg isopropanol and, after filtering to clarify, filled into 1,000 threaded containers with pump vaporizer caps.

EXAMPLE 2

Spray preparation containino DICLOFENAC 1 kg DICLOFENAC is dissolved, with warming, in 19 kg polyhydroxy fatty acid, commercially available as CETIOL HE, then mixed with 80 kg isopropanol and, after filtration, filled into 2,000 threaded containers with pump vaporizer caps.

EXAMPLE 3

Spray preparation containing DICLOFENAC 10 kg of copolymer, commercially available as Pluronic P 651, is dissolved in 89 kg ethanol and 1 kg DICLOFENAC is dissolved with warming in this mixture. After filtration the solution is filled into 2,000 threaded containers with pump vaporizer caps.

EXAMPLE 4

Spray preparation containino IBUPROFEN 2.5 kg IBUPROFEN are dissolved in 10 kg propylene glycol, then mixed with 37.5 kg isopropanol and, after filtration, filled into 1,000 threaded containers with pump vaporizer caps.

EXAMPLE 5

Spray preparation containing NAPROXEN-SODIUM 1.0 kg NAPROXEN-SODIUM is dissolved, with warming, in 20 kg of the polyhydroxy fatty acid used in example 2, then mixed with 79 kg isopropanol and, after filtration, filled into spray cans with addition of propellant.

"Volatile solvents" are those solvents whose vapor pressure is above 35 mm Mg when the skin temperature is 32° C., whereas "non-volatile solvents" are solvents whose vapor pressure is below 10 mm Mg at 32° C. skin temperature; Specifically suitable are solvents whose vapor pressure is below 5 mm Mg, specifically 1 to 2 mm Mg, when the skin temperature is 32° C.

While the invention has been described in terms of various preferred embodiments, one skilled in the art will appreciate that various modifications, substitutions, ommissions, and changes may be made without departing from the spirit thereof. Accordingly, it is intended that the scope of the present invention be limited solely by the scope of the following claims.

What is claimed is:

1. A sprayable preparation for topical application of pharmaceutical agents containing an effective amount of an arylalkanoic acid or its salts as the active agent, comprising a solvent mixture consisting of
    (a) at least one volatile, physiologically compatible solvent whose vapor pressure is above 35 mm Mg when the skin temperature is 32 degrees centigrade, and
    (b) at least one non-volatile physiologically compatible solvent whose vapor pressure is below 10 mm Mg at 32 degrees centigrade skin temperature, the weight ratio of a:b being from about 1:1 to 20:1.

2. The sprayable preparation according to claim 1, wherein the active agent is DICLOFENAC, FENOPROFEN, FLURBIPROFEN, IBUPROFEN, NAPROXEN or KETOPROFEN at a concentration ranging from about 0.1 to 10% by weight.

3. The sprayable preparation according to claim 1, wherein ethanol, propanol, or isopropanol is the volatile solvent.

4. The sprayable preparation according to claim 2, wherein ethanol, propanol, or isopropanol is the volatile solvent.

5. The sprayable preparation according to claim 1, wherein a polyfunctional alcohol, is the non-volatile solvent.

6. The sprayable preparation according to claim 2, wherein a polyfunctional alcohol, is the non-volatile solvent.

7. The sprayable preparation according to claim 5 wherein the polyfunctional alcohol is propylene glycol, glycerin, a liquid polyethylene glycol, or a polyoxyalkylene glycol.

8. The sprayable preparation according to claim 6 wherein the polyfunctional alcohol is propylene glycol, glycerin, a liquid polyethylene glycol, or a polyoxyalkylene glycol.

9. The sprayable preparation according to claim 1 wherein the non-volatile solvent is a fatty acid ester of a mono- or polyfunctional alcohol.

10. The sprayable preparation according to claim 2 wherein the non-volatile solvent is a fatty acid ester of a mono- or polyfunctional alcohol.

11. The sprayable preparation according to claim 1, further comprising a film forming material.

12. The sprayable preparation according to claim 11 wherein the film forming material is polyacrylate.

13. The sprayable preparation according to claim 2, further comprising a film forming material.

14. The sprayable preparation according to claim 13 wherein the film forming material is polyacrylate.

15. A method for the treatment of traumatic or rheumatic conditions in a warm-blooded animal comprising the topical administration of a functional amount of an active agent contained in the preparation of claim 1.

16. A method for the treatment of traumatic or rheumatic conditions in a warm-blooded animal comprising the topical administration of a functional amount of an active agent contained in the preparation of claim 2.

* * * * *